United States Patent [19]

Berejka

[11] Patent Number: 5,302,629

[45] Date of Patent: Apr. 12, 1994

[54] HYDROPHILIC ACRYLIC PRESSURE SENSITIVE ADHESIVES

[76] Inventor: Anthony J. Berejka, 4 Watch Way, Huntington, N.Y. 11743

[21] Appl. No.: 885,038

[22] Filed: May 15, 1992

[51] Int. Cl.$^5$ .................. C08L 33/08; C08L 33/10; C08L 33/14; C08F 20/26

[52] U.S. Cl. ..................... 523/111; 522/120; 522/183; 524/558; 525/303; 526/318.42; 526/320

[58] Field of Search ............... 523/111; 524/558; 526/318.42, 320; 522/120, 183; 525/303

[56] References Cited

U.S. PATENT DOCUMENTS

| | | | |
|---|---|---|---|
| 3,311,583 | 3/1967 | Bearden | 526/318.42 |
| 3,339,546 | 9/1967 | Chen | 523/111 |
| 3,370,050 | 2/1968 | Seiner | 526/320 |
| 3,763,117 | 10/1973 | McKenna, Jr. et al. | 526/320 |
| 3,840,390 | 10/1974 | Kozu et al. | 526/320 |
| 4,077,926 | 3/1978 | Sanderson et al. | 526/318.42 |
| 4,234,467 | 11/1980 | Ryrfors et al. | 526/318.42 |
| 4,379,864 | 4/1983 | Gallop et al. | 524/558 |
| 4,452,776 | 6/1984 | Refojo | 526/320 |
| 4,477,325 | 10/1984 | Osborn | 523/111 |
| 4,551,490 | 11/1985 | Doyce et al. | 523/111 |
| 4,563,184 | 1/1986 | Korol | 523/111 |
| 4,587,313 | 5/1986 | Ohta et al. | 526/320 |
| 4,618,390 | 10/1986 | Powell | 526/558 |
| 4,693,776 | 9/1987 | Krampe et al. | 523/111 |
| 4,737,559 | 4/1988 | Kellen et al. | 526/316 |
| 4,808,656 | 2/1989 | Kania et al. | 524/558 |
| 4,904,749 | 2/1990 | Bursky et al. | 526/328 |

FOREIGN PATENT DOCUMENTS

| | | | |
|---|---|---|---|
| 0103146 | 3/1984 | European Pat. Off. | 526/320 |
| 0103199 | 3/1984 | European Pat. Off. | 526/320 |
| 0164907 | 12/1985 | European Pat. Off. | 526/318.42 |
| 0045338 | 4/1978 | Japan | 524/558 |
| 0043585 | 9/1982 | Japan | 526/320 |
| 0064614 | 4/1984 | Japan | 526/320 |
| 0237181 | 10/1991 | Japan | 526/320 |

OTHER PUBLICATIONS

Pierson, Don "An Overview of Skin Contact Applications for Pressure-Sensitive Adhesives".
Lucast and Taylor "Crosslinked Acrylate Adhesives for Skin Use".
Satas, Don Handbook of Pressure Sensitive Adhesives Technology, pp. 397 to 402.

*Primary Examiner*—Paul R. Michl
*Assistant Examiner*—Peter Szekely

[57] ABSTRACT

Acrylic pressure sensitive adhesives which exhibit hydrophilicity and moisture permeability can be made by curing or crosslinking low molecular weight acrylic oligomers modified with substantial quantities of a hydroxyl containing monomer. The resultant modified pressure sensitive adhesive acrylic copolymers, upon crosslinking, will then have a hydrophilic hydroxy component incorporated into the copolymer backbone. Such adhesives are particularly useful in skin contact applications, such as the adhesives used on bandages or the adhesives used in transdermal drug delivery systems.

23 Claims, No Drawings

HYDROPHILIC ACRYLIC PRESSURE SENSITIVE ADHESIVES

HYDROPHILIC ACRYLIC PRESSURE SENSITIVE ADHESIVES

This invention relates to adhesives based on normally pressure sensitive polymers and copolymers made from $C_4$ to $C_{10}$ alkyl esters of acrylic acid wherein substantial quantities of hydroxyl groups have been incorporated through modification of prepolymers or oligomers of said acrylic alkyl esters with monomers such as hydroxy ethyl methacrylate (HEMA). Said hydroxyl addition renders the resultant copolymers hydrophilic and moisture permeable, features which are desirable, for example, in adhesives which are to be applied to skin for wound care purposes, and capable of enzyme immobilization and controlled release of bioactive agents.

BACKGROUND OF THE INVENTION

Diverse adhesive technologies have been used for skin contact applications. A review article by Pierson (*TAPPI Journal*, June 1990, pages 101 to 107) describes the broad range of approaches which have been taken to provide adhesive systems which will adhere to skin and have utility in a diverse number of areas.

One major category of such skin contact adhesives are compositions based on physical blends of hydropholic additives into normally pressure sensitive materials. For example, Chen in U.S. Pat. No. 5,339,546, Osburn in U.S. Pat. No. 4,477,325 and Doyle et al. in U.S. Pat. No. 4,551,490, all teach variations of this art. While effective in some applications, such physical blends suffer in that the hydrophilic additives are not chemically bound into the polymeric backbone. As a result, when becoming hydrated by the exudate of body fluids, such as perspiration, phase separation can occur. This leads to the formation of weak boundary layers and loss of adhesives properties. Further embodiments of this same technique of physically blending hydrophilic additives, such as hydrocolloid powders as powdered sodium carboxymethylcellulose (NaCMC), into a polymeric pressure sensitive adhesives as binders have been proposed, including the use of acrylic pressure sensitive materials as the polymeric binder. Further, the addition of other water soluble, but not chemically bound agents, such as low molecular weight polyols, as glycerol, have been proposed to enhance the rates of hydration (as in International Application WO 91/09633). These too suffer from not having the added hydrophilic agent chemically bound into the polymer system.

It has long been known that pressure sensitive adhesives can be produced from a variety of alkyl esters of acrylic acid. Polymers and copolymers based on $C_4$ to $C_{10}$ acrylic esters are inherently pressure sensitive and have a well established use in industry. The effects of monomer type and of the resultant molecular weight on pressure sensitive adhesive properties are well known to those skilled in the art. For instance, in the *Handbook of Pressure Sensitive Adhesive Technology*, Satas teaches how the chain length of a dependent alkyl group influences such properties as glass transition ($T_g$) and resistance-to-peel (pages 397 to 402). Numerous other publications can be found to further illustrate this well known technology.

Attempts to enhance the moisture permeation of acrylic pressure sensitive adhesives themselves have involved such techniques as aerating the adhesive as it is applied to a web and dried, creating a micro structure resembling a polymeric foam. Other attempts to enhance the hydrophilicity of acrylic pressure sensitive adhesives have involved the addition of monomers, such as n-vinyl pyrrolidone or acrylamide, during synthesis of the pressure sensitive adhesive, as discussed by Lucast and Taylor (*TAPPI Journal*, June 1990, pages 159 to 163). However, the use of said monomers pose toxicity concerns during manufacture and are often used in only relatively minor quantities. Furthermore, polymerization must be carried out in solvent media in order to adequately incorporate these monomers, which contribute to hydrophilicity, into the polymer backbone. The resultant polymer must then be cast from a solvent onto a web in order to create useful products. Such solvent casting techniques now pose environmental concerns over volatile organic emissions and have inherent production inefficiencies. Kellen et al. in U.S. Pat. No. 4,737,559 teaches that such solution polymerization techniques are common and well known in the art.

Hydroxy containing acrylic monomers have long been used in the manufacture of medical products. For example, polymerizates of hydroxy ethyl methacrylate (HEMA) are used in the manufacture of contact lenses. The resultant products made from pure HEMA are hard, brittle plastics which require some plasticization in order to yield functional materials. However, because of their hydroxy functionality, said products are inherently moisture permeable and susceptible to moisture pick-up and are thus inherently hydrophilic. Polymerization of HEMA itself is exceedingly sensitive to reactor conditions (as taught by Bursky et al. in U.S. Pat. No. 4,904,749). Because of the high charge transfer of its —OH group, polymerization of HEMA readily results in gel or partially crosslinked polymer networks and when not gelled poly-HEMA must often be stored under cool or refrigerated conditions to prevent further autopolymerization. Nonetheless, Korol in U.S. Pat. No. 4,563,184 teaches the value of polymerized HEMA adhesive systems as being efficacious in the delivery of certain drugs or bioactive components and in wound healing applications.

Attempts to incorporate HEMA or similar hydroxy containing monomers into acrylic pressure sensitives have, as a consequence, been limited to relatively small additions, say <5%, to the monomer make up of an adhesive polymerizate. Even at these relatively low concentrations, difficulties are encountered in attempting to control the kinetics of synthesis. Often an undesirable polymer gel results when attempting to synthesize conventional, inherently pressure sensitive acrylic copolymers based on $C_4$ to $C_8$ acrylic esters to which hydroxy containing monomers, such as HEMA, have been added. Such gels cannot be further processed or applied to webs or substrates as adhesive materials. Thus, the use of hydroxy containing monomers, such as HEMA, has been limited in the use of pressure sensitive adhesives for applications in which the hydrophilicity of HEMA like substitutive groups would be desirable, as for skin contact adhesives.

The chemical structures below are illustrative, but not necessarily inclusive, of the differences between conventional acrylic based pressure sensitive adhesives and the novel adhesives based on modifying a prepolymerized acrylic pressure sensitive precursor with hydroxy ethyl methacrylate.

Conventional emulsion and solution random acrylic pressure sensitive copolymers

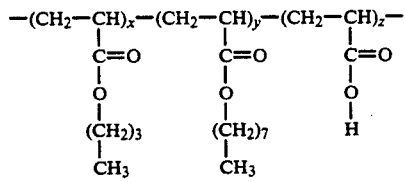

If $y>x$ (more 2-ethylhexyl acrylate or isooctyl acrylate than butyl acrylate), the greater the tack and the lower the cohesive strength. Acrylic acid, z, often ranges from 0 to 5% and creates hydrogen bonding between polymer chains to enhance cohesive strength and also promotes adhesion to polar substrates.

Novel hydrophilic acrylic pressure sensitive adhesives:

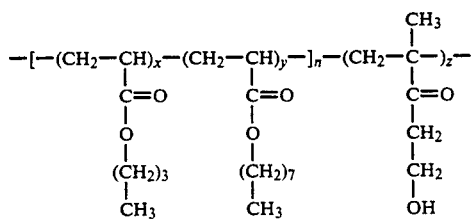

For example, homopolymers or random copolymer of butyl and/or 2-ethylhexyl acrylate are prepolymerized and in the form of a viscous liquid oligomer, wherein the molecular weight, as indicated by a number of repeat units, n, can be in the range of 1,000 to 150,000. Hydroxyethyl methacrylate (HEMA), which enhances hydrophilicity, moisture permeability and skin contact adhesion, can be incorporated at as high as the 40% level and will copolymerize into the homopolymer or random copolymer pressure sensitive oligomer base upon crosslinking or curing using any free radical source, such as those resulting through photoinitiation or, alternatively, exposure to electron beam ionizing irradiation.

SUMMARY OF THE INVENTION

It has been discovered that blends of an acrylic pressure sensitive adhesive oligomeric base, made from $C_4$ to $C_{10}$, acrylic ester monomers having a molecular weight $>1,000$, can be modified with substantial quantities, $>5\%$, but $<40\%$, of a hydroxy containing acrylic monomer, such as HEMA, to produce hydrophilic and moisture permeable pressure sensitive adhesives upon curing or crosslinking. Said cure can be initiated by conventional free radical sources, such as peroxide addition followed by thermal initiation, by photoinitiation via exposure to ultraviolet light or by exposure to ionizing irradiation from electron beams.

Said blends of $C_4$ to $C_{10}$ oligomeric bases with HEMA monomer can be easily made and then processed and coated directly onto webs as 100% non-volatile liquids and finally subjected to ultraviolet light or electron beam initiated curing and copolymerization. Unlike other monomers heretofore selected to impart hydrophilicity to acrylic pressure sensitives, HEMA is itself relatively non-toxic. For example, the oral toxicity of HEMA $LD_{50}$ is $>5,000$ mg/kg for rodents, whereas the toxicity of either acrylamide monomer, as proposed by Krampe et al. in U.S. Pat. No. 4,693,776, is $LD_{50}$ 170 mg/kg or n-vinyl pyrrolidone is $LD_{50}$ is 1.44 mg/kg. While suitable diluents for said acrylic pressure sensitive oligomer bases, neither acrylamide nor n-vinyl pyrrolidone could therefore be practically used in substantial quantities when such bases are designed to be applied as 100% non-volatile liquid precursors. Those skilled in the art will also realize that pendant hydroxyl groups pose less notable potential for skin irritation than the heretofore use of acid functionality which was achieved by incorporating acrylic acid into a polymer chain.

Thus in accordance with this invention, there is provided an adhesive composition comprising:

(a) an oligomer base made by the synthesis of $C_4$ to $C_{10}$ acrylic esters or similar acrylic esters having comparable pendant chain length having a molecular weight $>1000$ Daltons, or preferably an oligomer made from either n-butyl acrylate ($C_4$) or combinations with isooctyl or 2-ethyl hexyl acrylate ($C_8$) or mixtures thereof said oligomer base having a molecular weight $>1,000$ but $<150,000$ Daltons with said base being at most a viscous liquid at ambient temperatures;

(b) a diluent monomer with hydroxy functionality, preferably either hydroxy ethyl acrylate or optimally hydroxy ethyl methacrylate (HEMA) with said monomer present in quantities of mixtures thereof $>5\%$ but $<50\%$, preferably $>5\%$ and $<40\%$, e.g. at least 5% up to 25% by weight optimally at least 5% to 20%;

(c) optionally other diluent monomers, such as 2(2-ethoxyethoxy) ethylacrylate, a slightly water soluble monomer without hydroxy groups, or isodecyl acrylate but preferably either isooctyl acrylate or 2-ethyl hexyl acrylate which are used as diluents to both reduce application viscosity and to increase pressure sensitive tack after curing;

(d) optionally multifunctional monomers, such as difunctional and trifunctional acrylic monomers, preferably trimetylol propane triacrylate, which can be incorporated at modest levels, say up to 5% to enhance the cure rate of the adhesive composition or its response to photoinitiation or electron beam curing conditions;

(e) optionally a source for free radical initiation of cure by either the incorporation of peroxides which decompose on exposure to heat or photoinitiators which decompose on exposure to light, preferably in the ultraviolet range or by exposure to an electron beam, x-rays or gamma source.

Furthermore, it is provided a process for manufacture of a hydrophilic pressure sensitive adhesive which consists of:

(a) blending the aforementioned oligomers and monomers and, if desired, photoinitiators and/or other additives to form a liquid coating which is non-volatile at ambient temperatures;

(b) coating said liquid onto a moving web or other object;

(c) exposing said adhesive precursor to either ultraviolet light or to the ionizing irradiation from an electron beam to induce curing and copolymerization of the hydroxy moiety into the pressure sensitive adhesive.

Finally, articles such as bandages or other products wherein an inherently hydrophilic pressure sensitive adhesive would be of commercial value are envisioned applications for the above art. Because of the benign nature of the pendant hydroxyl groups, these adhesives are particularly suited for drug delivery systems. Said hydroxy functionality can be used to immobilize enzymatic and/or other bioactive agents, providing for controlled release upon hydration from body fluids and the like.

DETAILED DESCRIPTION OF THE INVENTION

Oligomer bases for coating onto webs or other objects and subsequently exposing such normally 100% non-volatile liquids to either ultraviolet light or electron beam irradiation are well known in the art. Of particular interest in the development of pressure sensitive adhesives are oligomeric bases produced by UCB Radcure. Specifically, UCB Radcure pressure sensitive adhesive bases IRR 84, IRR 85 and IRR 153, the former two being supplied with monomer diluents already present, the later being a non-diluted oligomer, i.e. a polymeric base of >1000 Daltons in molecular weight. The oligomers used in these materials are proprietary but based on $C_4$ to $C_8$ acrylic esters.

Hydroxy containing monomers suitable for use in these compositions are, for example, hydroxy ethyl methacrylate (HEMA), sold under the trade names of Sipomer CL-100 by Rhone-Poulenc or Rocryl 400 by Rohm and Haas.

To enhance the cure rate of blends of the oligomer bases diluted with the HEMA monomer, small quantities of a multifunctional acrylate, such as trimethylolpropane triacrylate sold by the Sartomer Company as SR-351, can be used.

When using ultraviolet light to promote cure and crosslinking, the preferred photoinitiator is 2-(4-(2-hydroxy-2-methyl-1-oxopropyl)phenoxyethyl)-2-propenoate having a formula of $C_{15}H_{18}O_5$ and sold under the designation of ZLI-3331, formerly by EM Industries, Inc. but now by the Ciba-Geigy Corporation. This photoinitiator is preferred since upon decomposition when exposed to ultraviolet light, its decomposition by-products graft into the polymer backbone, leaving no deleterious extractables.

The combinations of oligomer, monomers and photoinitiator described below can be easily blended together in a low shear mixer or, for experimental purposes, even by hand stirring. Because of the higher viscosity of the IRR 153 a slight amount of heating is needed to facilitate mixing, up to 50° C. was adequate when using this oligomeric base. Because the ZLI-3331 photoinitiator comes as a dried powder, some heating may also be need to incorporate this additive. However, the ZLI-3331 was found to be directly soluble in some preferred monomeric diluents.

These acrylic pressure sensitive adhesives can contain other ingredients as commonly used by those skilled in the art. For example, to enhance the tack of the cured or crosslinked adhesive it is preferred to add 2-ethyl hexyl ($C_8$) and/or isodecyl ($C_{10}$) acrylate monomers to the liquid blends. These too will cure or crosslink into the polymer matrix.

Electron beam irradiation, as generated, for example, from linear filament accelerators having a voltage potential of 150,000 to 300,000 volts, is suitable for copolymerizing the HEMA monomer into the base acrylic pressure sensitive without the use of photoinitiators or other additives.

When using photoinitiation, adequate cure could be obtained for 50 micron thick adhesive films with 300 watt/inch medium pressure mercury vapor ultraviolet lamps such as manufactured by American Ultraviolet. Electrodeless lamp systems, such as those manufactured by Fusion UV Curing Systems, were also found to be effective. In particular, tighter cure was obtained using the Fusion "D" bulb with a peak intensity in the near ultraviolet, 350 to 400 nm, than when using the Fusion "H" bulb, which has greater intensity in the far UV range, 200 to 325 nm range when running at comparable under lamp speeds. Good cure was achieved in air without the need for nitrogen inerting, as is sometimes practiced in the art.

EXAMPLE 1

The pressure sensitive oligomer composition IRR 84 from UCB Radcure, containing 47% of a $C_4$ to $C_8$ acrylic ester oligomeric copolymer and 53% of a mixture of monomeric diluents, such as 2-ethylhexyl acrylate, isobornyl acrylate and 4% n-vinyl-2-pyrrolidone was mixed with 5% of the ZLI-3331 photoinitiator as a control. A similar composition was made with 20% HEMA monomer added to the mixture as below:

TABLE I

|  | Control 1 | A |
|---|---|---|
| IRR 84 acrylic oligomer | 95% | 75% |
| Sipomer CL-100 HEMA monomer | — | 20% |
| ZLI-3331 photoinitiator | 5% | 5% |

Hand draw downs were made onto a release coated paper using a Meyer rod to achieve approximately 50 microns thick wet coating. These were then passed under an American Ultraviolet laboratory curing unit with the conveyor set at 25 feet/minute using a 300 watt/inch medium pressure mercury vapor ultraviolet source. Tactile evaluation indicated that the control sample, without any HEMA monomer, cured well on one pass and could be transferred from the release paper to a polyethylene or polyurethane film without difficulty. Sample A with the 20% HEMA content, required four passes to achieve the same cure. This was not unexpected since additional monomer often retards the cure rate of ultraviolet activated systems.

When comparing the Control 1 and Compound A as skin contact adhesives, the HEMA containing adhesive remained in contact with the forearm without lifting over a several day period of wear. The non-HEMA UV cured acrylic Control 1 remained in contact with skin for only a few hours and lifted easily of its own accord.

EXAMPLE 2

Laminates of these adhesives were made to the breathable, high moisture vapor transmission rate (MVTR) Exxaire 10B04 film which is available from the Exxon Chemical Company. These were tested to demonstrate the effects of HEMA modified acrylic pressure sensitive on MVTR or the ability to pass moisture through them. Tests were run per ASTM E-96 using the inverted cup method. Several additional samples based on the background art are included by way of example.

TABLE II

| Moisture Vapor Transmission Rate Data | g/m²/24 hrs @ 40° C. |
|---|---|
| Exxaire 10B04 breathable film (control) | 5400 |
| Exxaire + Sample A = IRR 84 with 20% HEMA | 500 |
| Exxaire + 2 mils hot melt adhesive | 35 |
| Exxaire + 30 mils hydrocolloid containing | 25 |

TABLE II-continued

| Moisture Vapor Transmission Rate Data | g/m²/24 hrs @ 40° C. |
|---|---|
| hydrophilic adhesive per US 4,551,490 | |

From this data it is apparent that the HEMA modified pressure sensitive acrylic is more moisture permeable, even than those adhesives containing hydrocolloids, which are well known in the trade for their hydrophilicity and their skin contact properties.

EXAMPLE 3

Of concern in the medical products field and in the manufacture of bandages is the effects of sterilization conditions on adhesive properties. The Control 1 and Compound A from Example 1 were cured using ultraviolet light per the example and again transfer laminated to the Exxaire breathable film. These were then subjected to electron beam irradiation at 2.5 Mrads, a typically prescribed sterilization dose, and to 5.0 Mrads using a 4.5 MeV Dynamitron accelerator.

Probe tack (ASTM D-2979) results confirmed that these systems remain adhesive even after electron beam sterilization. Using probe conditions of 100 g/cm² load, 1 second dwell and 1 cm/sec separation rate, the following results were obtained for these adhesives:

TABLE III

| Adhesive | Film | EB dose | Probe Tack |
|---|---|---|---|
| Control 1 | Exxaire 10B04 | none | 30 g |
| Control 1 | Exxaire 10B04 | 2.5 Mrad | 70 g |
| A | Exxaire 10B04 | none | 350 g |
| A | Exxaire 10B04 | 2.5 Mrad | 90 g |
| A | Exxaire 10B04 | 5.0 Mrad | 60 g |

The HEMA modified acrylic pressure sensitive retains a reasonable tack even after electron beam sterilization. The tack of composition A is comparable to the Control 1 prior to sterilization.

EXAMPLE 4

A pure acrylic pressure sensitive oligomer not containing monomer diluents based on $C_4$ to $C_8$ acrylic esters was evaluated, UCB Radcure's IRR 153. Comparisons were made to determine the uniqueness of the hydroxyl acrylic monomer addition, HEMA, and to determine the effects of polyfunctional acrylates on the rate of ultraviolet curing. The four compositions below were prepared by heating the viscous IRR 153 and then adding the powdered photoinitiator and then the monomeric diluents. 2(2-ethoxyethoxy) ethylacrylate was used as a comparative, slightly water soluble monomer without hydroxy groups. This is available from the Sartomer Company as SR-256.

TABLE IV

| | Control 2 | B | C | D |
|---|---|---|---|---|
| IRR 153 acrylic oligomer | 95% | 75% | 75% | 75% |
| Rocryl 400 HEMA monomer | — | 20% | 17% | — |
| Sartomer TMPTA SR-351 | — | — | 3% | — |
| Sartomer EOEOEA Sr-256 | — | — | — | 20% |
| ZLI-3331 photoinitiator | 5% | 5% | 5% | 5% |

These compositions were drawn down onto release coated polyester film using a Bird applicator to achieve approximately 50 microns wet film thickness. Samples were then passed under an American Ultraviolet laboratory curing unit with the conveyor set at 20 feet/minute using a 300 watt/inch medium pressure mercury vapor ultraviolet source. Tactile evaluation indicated that the Control 2 sample, without any HEMA monomer, cured well on one pass and could be transferred from the release paper to the breathable polyethylene Exxaire film without difficulty. Compound B with the 20% HEMA content, required but two passes to achieve the same relative cure. In contrast to Compound A in Example 1, this higher cure rate reflects the lower overall monomer content in this composition. As might be expected, Compound C, with the polyfunctional acrylate added, cured tightly in only one pass, even with a high content of HEMA monomer in it. Compound D also cured in only one pass at 20 feet/minute, since the EOEOEA monomer is known for its reactivity.

Transfer laminates made to the breathable polyethylene film were applied to the forearm and evaluated for skin adhesion. Both Compound B and the faster curing Compound C, which contained substantial quantities of HEMA copolymerized into the cured pressure sensitive adhesive polymer, remained in contact for several days with no lifting or loss of adhesion. In contrast, Compound D, without pendant hydroxyl groups, lost adhesion to skin and lifted in a matter of hours.

To those skilled in the art, embellishments of the above described acrylic pressure sensitive adhesives would be apparent. For example, isooctyl or 2-ethyl hexyl acrylates ($C_8$) or isodecyl acrylate ($C_{10}$) can be added as diluents to enhance the pressure sensitive tack. Balances between the oligomer base, IRR 153, HEMA, other monofunctional monomers used to enhance tack and polyfunctional monomers used to increase cure rate and the levels and types of photoinitiators, if ultraviolet curing is to be used, can be tailored for specific end use applications. Because of the low temperature curing of both ultraviolet light and electron beam systems, temperature sensitive bioactive ingredients, such as enzymes, can be incorporated into these adhesive compositions prior to curing for subsequent release upon hydration by body fluids. Other bioactive materials can also be contained in the uncured, liquid adhesive precursor for release upon application to skin or body parts.

What is claimed is:

1. A pressure sensitive, insoluble adhesive composition comprising the reaction product of (a) an oligomeric precursor made predominately from $C_4$ to $C_{10}$ alkyl esters of acrylic acid, and (b) a hydroxy containing monomeric moiety having vinyl functionality capable of coreacting with said oligomeric base wherein the oligomeric precursor has a molecular weight of greater than 1,000 Daltons.

2. An adhesive composition according to claim 1 wherein the hydroxy containing monomeric moiety is an acrylic monomer.

3. An adhesive composition according to claim 2 wherein the hydroxy containing monomeric moiety is hydroxy ethyl acrylate, hydroxy ethyl methacrylate or mixtures thereof.

4. An adhesive composition according to claim 1 wherein the hydroxy containing monomeric moiety is present by at least 5% up to 50% by weight as required to impart hydrophilicity or measurable water absorption of greater than 1% by weight.

5. An adhesive composition according to claim 4 wherein the hydroxy containing monomeric moiety is present in an amount of at least 5% up to 25% by weight.

6. An adhesive composition according to claim 1 wherein multifunctional acrylates are added to enhance cure response.

7. An adhesive composition according to claim 1 wherein photoinitiators are incorporated to promote free radical crosslinking and curing upon exposure to light.

8. An adhesive composition according to claim 1 wherein materials which decompose to generate free radical initiation are included.

9. An adhesive composition according to claim 1 wherein additives are included and wherein said additives are fillers, diluents, other reactive monomers, or hydrocolloid materials.

10. An adhesive composition according to claim 1 wherein bioactive materials are incorporated into the adhesive composition, wherein said bioactive materials are enzymes or drugs.

11. A solventless process for producing an adhesive composition which is an insoluble, gelled polymer network which comprises exposing a reaction mixture comprising (a) an oligomeric precursor consisting essentially of $C_4$ to $C_{10}$ alkyl esters of acrylic acid and (b) a hydroxy containing monomeric moiety having vinyl functionality capable of coreacting with said oligomeric base, to a source of radiant energy wherein the oligomeric precursor has a molecular weight of greater than 1,000 Daltons.

12. The process according to claim 11 wherein the hydroxy containing monomeric moiety is an acrylic monomer.

13. The process according to claim 12 wherein the hydroxy containing monomeric moiety is hydroxy ethyl acrylate, hydroxy ethyl methacrylate or mixtures thereof.

14. The process according to claim 11 wherein the hydroxy containing monomeric moiety is present in an amount of at least 5% up to 50% by weight.

15. The process according to claim 14 wherein the hydroxy containing monomeric moiety is present in an amount of at least 5% up to 25% by weight.

16. The process according to claim 11 wherein multifunctional acrylates are added to enhance cure response.

17. The process according to claim 11 wherein photoinitiators are incorporated to promote free radical crosslinking and curing upon exposure to light.

18. The process according to claim 11 wherein materials which decompose to generate free radical initiation are included.

19. The process according to claim 11 wherein fillers, diluents, other reactive monomers, or hydrocolloid materials are added.

20. The process according to claim 11 wherein bioactive additives are incorporated into the reaction mixture.

21. A process for producing a gelled polymer network of the adhesive composition according to claim 11 wherein said polymer gel has the hydroxy moiety incorporated into the polymer network.

22. The process according to claim 11 wherein the reaction mixture is exposed to ionizing irradiation where the iononizing irradiation source is an electron beam, gamma source or x-ray source.

23. The process according to claim 11 which consists of exposing the reaction mixture to electromagnetic energy in the form of light, radiofrequency or microwaves.

* * * * *